(12) United States Patent
Patel

(10) Patent No.: US 11,690,663 B1
(45) Date of Patent: Jul. 4, 2023

(54) DIRECTIONAL CRYOABLATION SYSTEM

(71) Applicant: Focused Cryo, Inc., Marietta, GA (US)

(72) Inventor: Yogi A. Patel, Marietta, GA (US)

(73) Assignee: FOCUSED CRYO, INC., Marietta, GA (US)

( * ) Notice: Subject to any disclaimer, the term of this patent is extended or adjusted under 35 U.S.C. 154(b) by 0 days.

(21) Appl. No.: 17/979,963

(22) Filed: Nov. 3, 2022

(51) Int. Cl.
A61B 18/02 (2006.01)
A61B 18/00 (2006.01)

(52) U.S. Cl.
CPC .... *A61B 18/02* (2013.01); *A61B 2018/00083* (2013.01); *A61B 2018/00095* (2013.01); *A61B 2018/00101* (2013.01); *A61B 2018/00678* (2013.01); *A61B 2018/00708* (2013.01); *A61B 2018/00744* (2013.01); *A61B 2018/00797* (2013.01); *A61B 2018/0243* (2013.01)

(58) Field of Classification Search
CPC .......... A61B 18/02; A61B 2018/00101; A61B 2018/00678; A61B 2018/00708; A61B 2018/00797; A61B 2018/0243
See application file for complete search history.

(56) References Cited

U.S. PATENT DOCUMENTS

| | | | | |
|---|---|---|---|---|
| 6,176,857 B1* | 1/2001 | Ashley | ................... | A61B 18/08 606/41 |
| 7,942,870 B2 | 5/2011 | Berzak et al. | | |
| 2006/0004351 A1* | 1/2006 | Arless | ................... | A61B 18/02 606/41 |
| 2008/0051774 A1* | 2/2008 | Ofir | ........................ | A61B 18/02 606/20 |
| 2008/0125764 A1 | 5/2008 | Vancelette et al. | | |
| 2011/0306904 A1* | 12/2011 | Jacobson | ........... | A61B 18/1492 606/1 |
| 2014/0316398 A1* | 10/2014 | Kelly | ..................... | A61B 18/02 606/24 |
| 2015/0025514 A1* | 1/2015 | Carl | ........................ | A61B 18/02 606/21 |
| 2015/0119868 A1* | 4/2015 | Lalonde | ................. | A61B 18/14 606/21 |
| 2016/0206373 A1* | 7/2016 | Chen | ..................... | A61B 5/0084 |
| 2016/0338752 A1* | 11/2016 | Sperling | ................ | A61B 90/04 |

* cited by examiner

Primary Examiner — Daniel W Fowler
(74) Attorney, Agent, or Firm — Tarolli Sundheim Covell & Tummino LLP

(57) ABSTRACT

A cryoablation system is provided that can assume a directional activated state and includes a cryoablation probe and a controller. The cryoablation probe has an active region that includes a cooling compartment and an opposing heating compartment that are thermally insulated from one another to minimize energy losses therebetween such that ice is selectively and directionally formed at the target site. The cooling compartment can include a temperature sensor and an exhaust tube to guide a fluid or gas that exhibits a Joule Thomson cooling effect through the probe. The heating compartment can include a temperature sensor and a heater cartridge having a heater zone. The controller of the cryoablation system can process temperature measurement data from the sensors of the heating and cooling compartments and regulate the heater zone based on the temperature measurement data processing to maintain a temperature that is sufficiently constant to mitigate or prevent formation of ice on the heating compartment.

20 Claims, 7 Drawing Sheets

DIRECTIONAL CRYOABLATION SYSTEM

TECHNICAL FIELD

The present application generally related to a directional cryoablation system.

BACKGROUND

Cryoablation is a procedure in which a liquid or gas is used to freeze and destroy abnormal tissue. Cryoneurolysis is the deliberate freezing of a nerve to induce a reversible ablation of the nerve and mitigate subsequent nerve regeneration. The recent combination of cryoneurolysis science and imaging (e.g. computed tomography, fluoroscopy, ultrasound, etc.) guidance has resulted in a myriad of minimally invasive procedures targeting nerves throughout the body for pain management, for example, without the need for opioids or high-risk procedures. Currently, operators interested in performing cryoneurolysis use tumor cryoablation probes, which are small (approximately less than 2.4 millimeters (mm)) diameter metal needles with symmetrically placed internal components and energy flowing linearly through the needle to maximize the region of tissue ablated. These needle-like probes are designed to destroy tumor cells, which requires temperatures colder than approximately −40° C. The probe is inserted into the tumor and high pressure gas, such as argon gas, is allowed to flow into the needle. The surrounding volume is cooled as the argon gas expands (Joule-Thomson (JT) effect), resulting in an oval shaped ablation zone that engulfs the tumor in approximately −140° C. ice. Gas flow is turned on and off to induce osmotic gradient shifts resulting in cell lysis and tumor breakdown. This effect is reliable in tumor cryoablation because the probe is inserted into tissue and the damage is non-discrete and wide.

This method differs from the needs of cryoneurolysis, where the probe cannot be inserted into the nerve because the probe could cause unwanted mechanical damage and pain. Moreover, an appropriate temperature to induce formation of ice microcrystals within the nerve membrane is approximately −20° C. for generally a minimum of ten minutes. When performing cryoneurolysis, the probe is generally placed parallel to the target nerve which introduces multiple challenges using existing probes including non-target damage, imprecise inclusion of the target nerve in the ablation zone, and unpredictable and unknown in vivo target tissue temperatures. This can lead to serious adverse consequences including post-procedure pain, organ damage and even death.

Success of cryoneurolysis procedures is tightly coupled to exposing the target nerve to the correct amount of cold temperature for the correct amount of time. If the temperature is too cold and the duration is too long, an irreversible nerve ablation is achieved and the patient may suffer permanent nerve loss. If the temperature is not cold enough and the duration is too short, a partial ablation may occur, resulting in a reduced or absent therapeutic benefit.

Presently, an operator interested in measuring target tissue temperature during ablation procedures generally inserts a second probe in the vicinity of the target tissue. However, it is difficult to insert this second probe because of difficulty associated with placing the second probe correctly, the increase in procedure time, and the increased risk of damage to the patient. Alternatives to inserting a second probe are to rely on gel isotherm data from benchtop testing or computational estimates based on the core probe temperature. These approaches assume ideal conditions and have been shown to be different from the actual temperatures achieved in patients. As such, there is a need to obtain actual target tissue temperature measurements when performing a cryoablation procedure.

Further, a key barrier to achieving the necessary cold exposure is accounting for inter-patient variability in body mass index and composition. The larger the body mass index, the greater the heat load on the device placed within the patient. This results in unpredictable and variable ablation zones and therapeutic outcomes. As such, there is a need for controlling the ablation zone temperature when performing a cryoablation procedure, In addition, a goal of a cryoneurolysis procedure is to ablate the target nerve while sparing surrounding structures. This is difficult to achieve with current tumor ablation devices, which create a large oval shaped cryozone (e.g. region of ice formation) that ablates all nearby target (e.g. nerve) and non-target (e.g. organ, bone, muscle) structures. Damage to non-target structures is common and has been shown to result in additional post-procedural pain and even death. Protection techniques such as hydrodissection, carbon dioxide pneumodissection, and balloon interposition can be used. In particular, a current clinical practice for reducing non-target damage is to move the non-target structure away from the target tissue by injecting air or saline at the site. However, this approach is cumbersome and requires constant monitoring and repositioning as the injected air or fluid disperses. Furthermore, any significant movement of the probe requires re-imaging to assess the probe's position. All of the above-mentioned techniques can increase procedure time, radiation exposure, and can impact the probe's performance. As such there is a need for an alternative modality to avoid non-target damage when performing a cryoablation procedure.

SUMMARY

A cryoablation system is provided herein that can assume a directional activated state and a non-directional activated state. The cryoablation system can comprise a cryoablation probe (referred to herein also as a "probe") and a controller. The cryoablation probe can be configured to ablate a target site and can comprise a shaft having an outer surface, an inner surface, a distal portion, a proximal portion, a first side, and a second opposing side. The probe can comprise an active region at the distal portion of the shaft. The active region can comprise a cooling compartment located at the first side of the shaft and a heating compartment located at the second opposing side of the shaft. The cooling and heating compartments can be thermally insulated from one another to minimize energy losses therebetween such that ice is selectively formed at the target site in a directional activated state of the cryoablation system. The cooling compartment can comprise an exhaust tube comprising a capillary tube disposed therein and configured to guide a fluid or gas that exhibits a Joule Thomson cooling effect through the shaft. A heat exchanger coil can be disposed over the capillary tube. The cooling compartment can further comprise at least one temperature sensor disposed adjacent to the exhaust tube. The heating compartment can comprise a heater plate, at least one temperature sensor disposed adjacent to the heater plate, and a heater cartridge located between the exhaust tube and the heater plate. The heater cartridge can comprise a heater zone. The cryoablation system can further include a controller operably connected to the cryoablation probe. The controller can comprise a processor and a memory. The memory can have computer-executable instructions stored thereon that, when executed by the processor, cause the controller to process temperature measurement data from the at least one sensor of the heating compartment and the at least one sensor of the cooling compartment and regulate the heater zone of the heater cartridge based on the temperature measurement data processing to maintain a temperature that is sufficiently constant to mitigate or prevent formation of ice on the heating compartment in a directional activated state of the cryoablation system.

DETAILED DESCRIPTION

Figure 1:
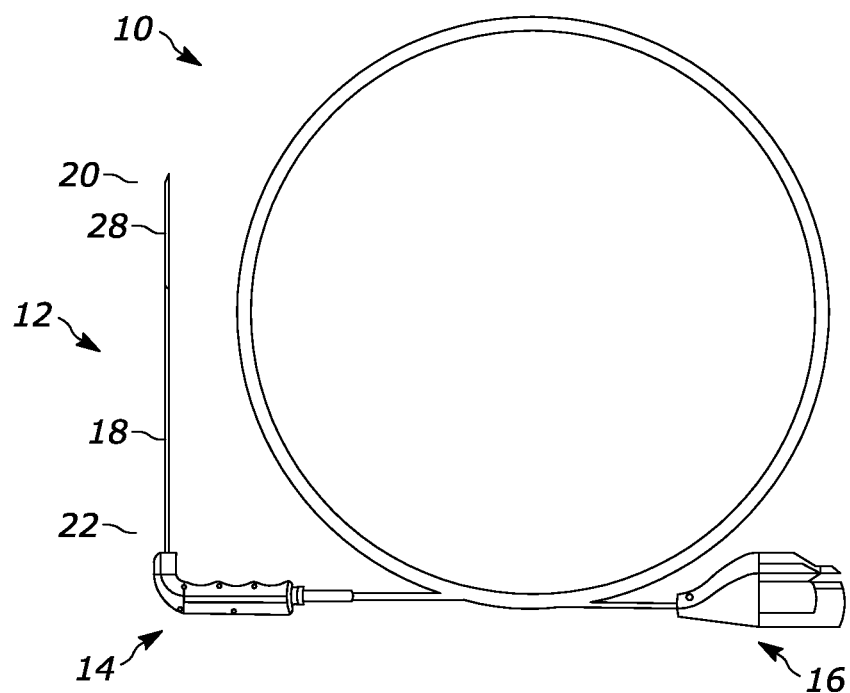
FIG. 1 is a top view of a cryoablation probe according to an aspect of the present disclosure.

The present disclosure relates to cryoablation probes and cryoablation systems, which include cryoneurolysis probes and systems. As used herein with respect to a described element, the terms "a," "an," and "the" include at least one or more of the described element(s) including combinations thereof unless otherwise indicated. Further, the terms "or" and "and" refer to "and/or" and combinations thereof unless otherwise indicated. By "substantially" is meant that the distance, shape, or configuration of the described element need not have the mathematically exact described distance, shape, or configuration of the described element but can have a distance, shape, or configuration that is recognizable by one skilled in the art as generally or approximately having the described distance, shape, or configuration of the described element. As such "substantially" refers to the complete or nearly complete extent of a characteristic, property, state, or structure. The exact allowable degree of deviation from the characteristic, property, state, or structure will be so as to have the same overall result as if the absolute characteristic, property, state, or structure were obtained. The terms "first," "second," etc. are used to distinguish one element from another and not used in a quantitative sense unless indicated otherwise. Thus, a "first" element described below could also be termed a "second" element. A component "connected to," "operably connected to," "disposed adjacent to," "disposed between," "disposed on." "located between," "located at" another component can have intervening components between the components so long as the cryoablation system can perform the stated purpose. The sequence of operations (or steps) is not limited to the order presented in the claims or figures unless specifically indicated otherwise. As used herein a "patient" includes a mammal such as a human being. Although the drawings show certain elements of a cryoablation system and cryoablation probe in combination, it should be noted that such elements can be included in other embodiments or aspects illustrated in other drawings. In other words, each of the disclosed aspects and embodiments of the present disclosure may be considered individually or in combination with other aspects and embodiments of the disclosure.

A cryoablation system is provided herein that can be used to freeze and destroy diseased tissue including ablating nerves. The cryoablation system addresses key challenges associated with monitoring the ablation zone temperature and minimizing non-target damage, for example. In particular, a cryoablation system as disclosed herein can provide actual target tissue temperature measurements from the cryoablation probe itself allowing control of the temperature and duration of the delivered cold energy without the need for a second needle insertion, can control the ablation zone temperature using an integrated tissue temperature measurement system and real-time temperature-based feedback, can generate directional cryozones without affecting surrounding tissue, generate specific ablation zone shapes and sizes for various indications regardless of the ablation energy modality, prevent or mitigate bridging, and/or control the rate and flow of energy to maximize energy transfer into the target tissue and minimize non-target damage. It should be noted that "bridging," in general refers to bridging via the tissue or bridging via the probe. Bridging via the tissue occurs when the generated ice from both edges of the cooling compartment extends into the tissue and connects to each other, resulting in ice located radially outward from the heater compartment. This results in ice wrapped around the heating compartment (but not necessarily forming on the heating compartment). Temperature measurement detected by a sensor (discussed below) of the heating compartment can have a signature profile that can be used to detect bridging. For example, when the sensor indicates that there is a gradual drop in temperature, this can indicate that bridging via the tissue is occurring and the heater cartridge is overpowered by the cooling energy of the cooling compartment and this can trigger a process to recover directional ice formation adjacent to the cooling compartment. Bridging via the probe occurs when the cooling compartment overpowers the heater cartridge and ice forms directly on the surface of the probe by conducting cooling energy through the outer surface of the probe. The temperature measurements of the sensor (discussed below) of the heating compartment can have a signature profile that can be used to detect bridging. For example, when the sensor indicate that there is a rapid drop in temperature, this can indicate that bridging via the probe is occurring and the heater cartridge is overpowered by the cooling energy of the cooling energy of the cooling compartment and this can trigger a process to recover directional ice formation.

In general, a cryoablation system can include a handle that an operator can grasp to manipulate a cryoablation probe, a vacuum tube for preventing freezing of non-active regions of the cryoablation probe, an exhaust tube for allowing a fluid or gas that exhibits a Joule Thomson cooling effect to flow back out of the cryoablation probe, electromagnetic sensors in the cryoablation probe for tracking the cryoablation probe positions, a copper coil array that acts as a heat exchanger to increase the cooling power of the cryoablation probe, a heater cartridge and heater plate for generating and supplying heat to create thermal gradients for directionality, thermocouples or other thermal sensors for measuring temperatures at specific points to ensure successful directional ablation zones, a gas connector that is used to flow pressurized gas through the cryoablation probe, and an electrical connector for mating the cryoablation probe to the electronics of a control console and probe configuration programming and identification.

Figure 2:
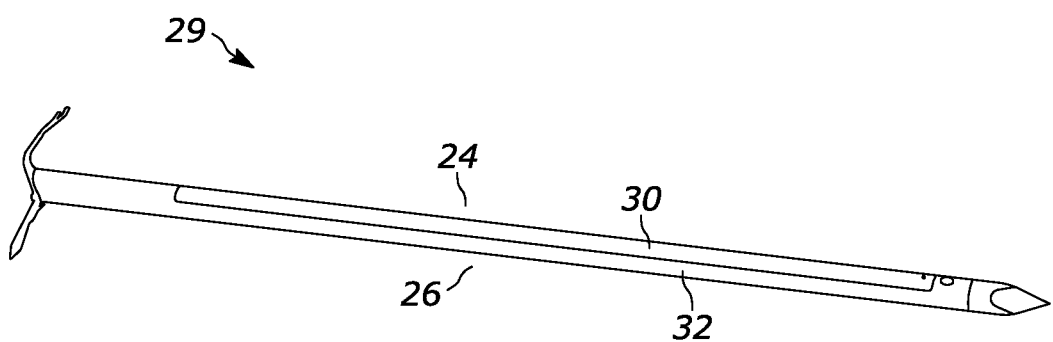
FIG. 2 is a side view of the active region of a cryoablation probe according to an aspect of the present disclosure.
Figure 3:
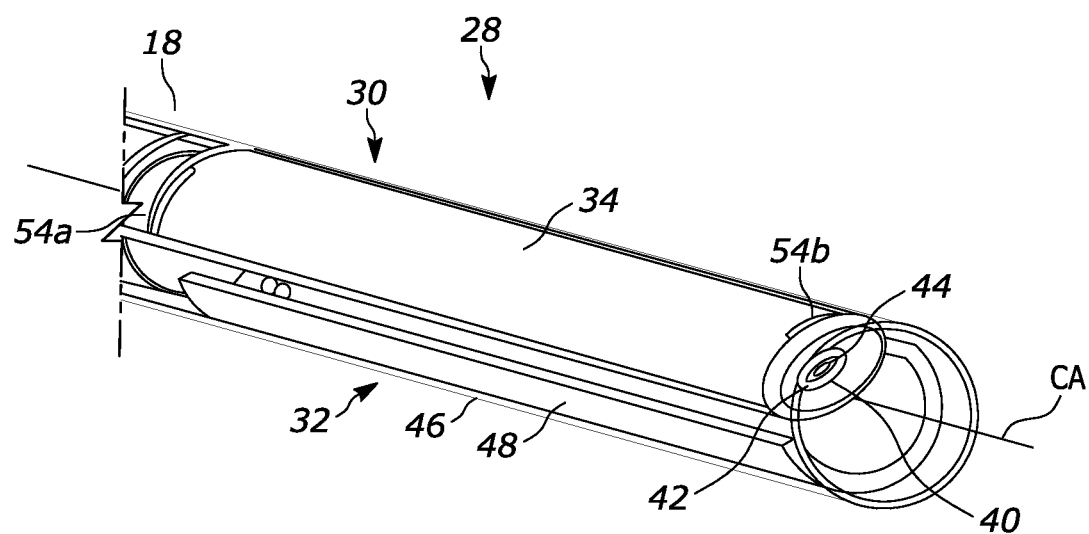
FIG. 3 is a perspective view of the active region of a cryoablation probe illustrating internal components of the active region of a cryoablation probe according to an aspect of the present disclosure.
Figure 4:
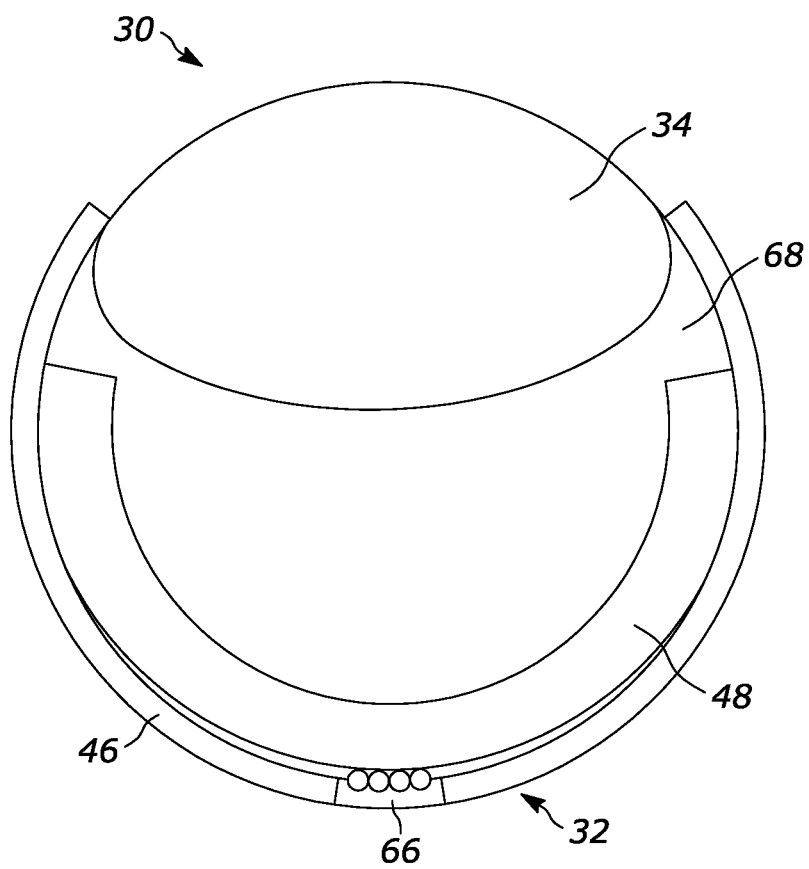
FIG. 4 is cross-sectional view of the active region of a cryoablation probe according to an aspect of the present disclosure.
Figure 12:
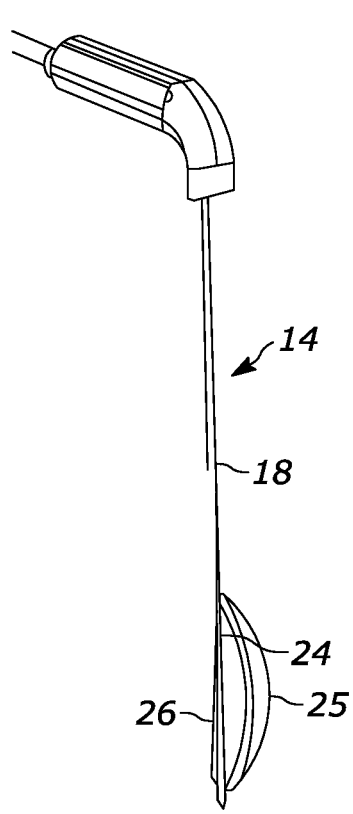
FIG. 12 is a schematic illustration of directional ice formation after activation of a cryoablation probe.
Figure 13:
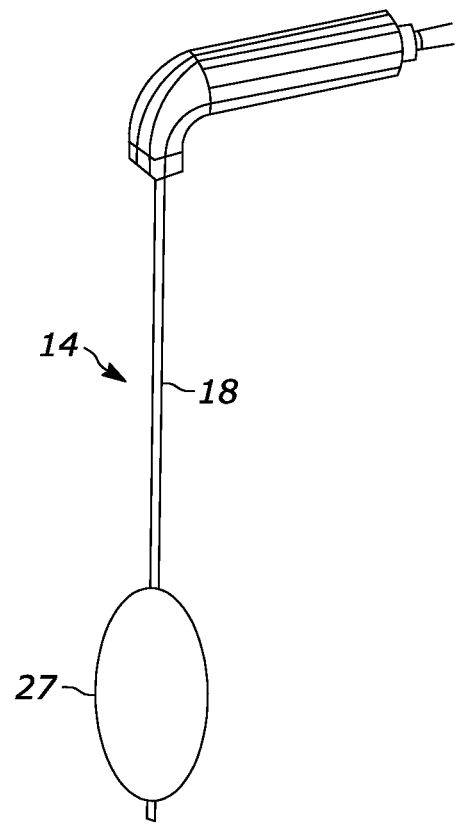
FIG. 13 is a schematic illustration of circumferential ice formation after activation of a cryoablation probe.

In particular and with reference to FIGS. 1 and 2, a cryoablation system 10 can include probe 12, handle 14, connector 16 and a controller (not shown). Probe 12 can comprise shaft 18 having distal portion 20, proximal portion 22, first side 24, and second opposing side 26. The probe can be a needle having a diameter between about 1.5 mm to about 3.5 mm. Other diameters are also possible. Distal portion 20 can include active region 28 which, when activated, can create a cryozone(s) in the patient's tissue. The active region can include mixed heating and cooling compartments that can create cryozone(s) that are directional and configurable (e.g. a cryoablation temperature can be obtained on one side of the probe while the other side is maintained at near body temperatures). In particular and with reference to FIGS. 2 and 3, active region 28 can comprise cooling compartment 30 located on first side 24 of shaft 18 and heating compartment 32 located on second side 26. With further reference to FIG. 12, in a directional activated state of the cryoablation system, ice (e.g. a cryozone) 25 is formed on or about first side 24 of active region 28 of shaft 18 and not on or about second side 26 of active region 28 of shaft 18. The directional cryozones can extend approximately 1.5 cm to approximately 2.0 cm laterally from the center of the probe. Such values are only exemplary and the directional cryozones can extend other distances. Referring to FIG. 13, in a non-directional activated state of the cryoablation system, the heating compartment is not activated and ice 27 formation is not limited to on or about first side 24 of active region 28 of shaft 18 and can form, for example, circumferentially on or about the active region of the probe. Referring to FIGS. 3 and 4, cooling compartment 30 and heating compartment 32 can be spaced from one another a distance D. The heating and cooling compartments are thermally insulated from one another to minimize energy losses therebetween such that ice is selectively formed at the target site in a directional activated state of the cryoablation system. The heater compartment can be disposed radially outward from central axis CA extending through the shaft. The cooling compartment and the heating compartment can be thermally insulated from one another to minimize energy losses such that ice is formed less than 360° about the cryoablation probe in a directional activated state of the cryoablation system.

Referring to FIG. 3, cooling compartment 30 can comprise an exhaust tube 34 configured to guide a fluid or gas that exhibits a Joule Thomson cooling effect through shaft 18. The fluid or gas can be any appropriate fluid or gas that can exhibit a Joule Thomson cooling effect such as, for example, argon, nitrogen, or oxygen. The exhaust tube can have a plugged distal end to contain all gas flow within the exhaust tube. In particular and with reference to FIG. 6, an open-ended capillary tube 44 can be disposed in the interior of exhaust tube 34. A heat exchanger coil can be disposed over the capillary tube. A pressurized cryogenic gas or fluid can flow from a control console (connected to a cryogenic gas or fluid source) and into the probe shaft via capillary tube 44. When the gas or fluid exits the capillary tube, the pressurized gas or fluid expands and the pressure of the gas or fluid decreases. The gas or fluid then travels back to the control console through the inner lumen of the exhaust tube and exhausts to ambient surroundings. This pressure decrease leads to a change in kinetic energy and is described by the Joule-Thomson effect. As the gas expands, pressure of the gas or fluid decreases, a rapid drop in the temperature of the surrounding area (inside and outside of the probe) occurs. This cooling causes the water content of the nearby tissue to freeze, resulting in ice formation.

Figure 5:
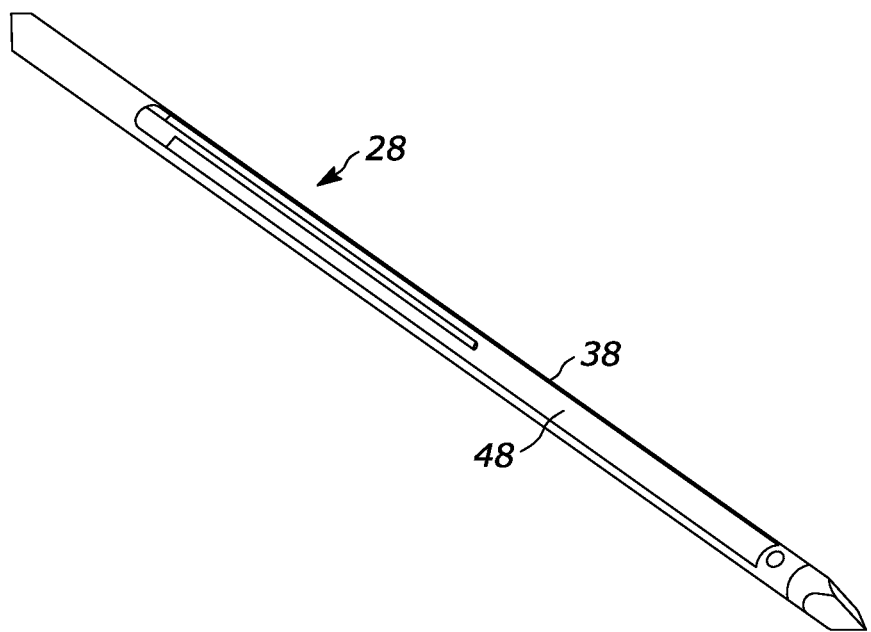
FIG. 5 is a top view of cryoablation probe illustrating a window of the cooling compartment of a cryoablation probe according to an aspect of the present disclosure.
Figure 6:
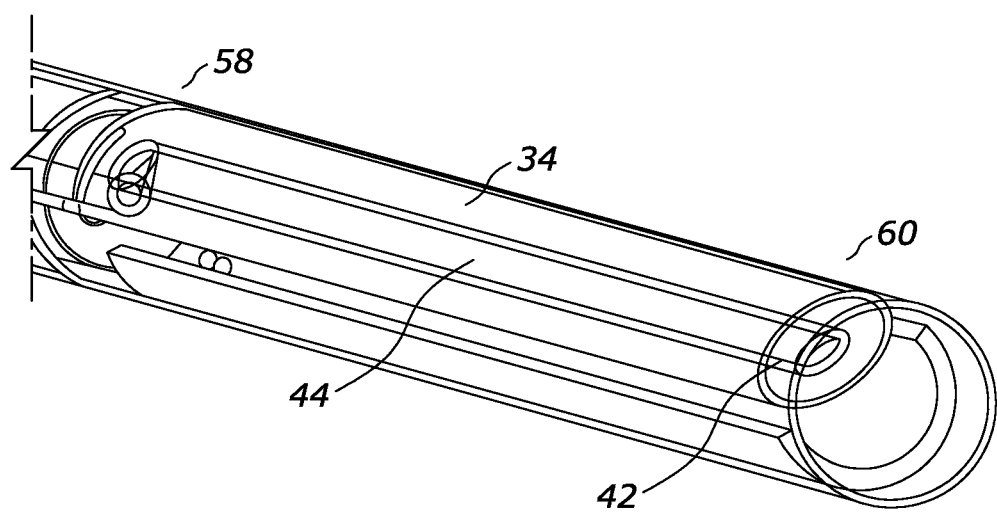
FIG. 6 is a perspective view of the active region of a cryoablation probe illustrating internal components of the action region of the cryoablation probe according to an aspect of the present disclosure.

Referring to FIGS. 2, 4 and 5, the shaft at the first side of the active region of the cryoablation probe can define an open window 38, exhaust tube 34 disposed within open window 38. This allows the exhaust tube to be directly exposed to the target tissue site. The window can extend less than 180° about the active region of the shaft of the cryoablation probe to control and constrain the "reach" of ice generation. As depicted in FIGS. 3, 4 and 6, exhaust tube 34 can comprise a substantially oval cross-sectional shape. An oval-shaped exhaust tube 34 can reduce the diameter of the exhaust lumen 40 when coupled with copper coil 42 and allow sufficient contact of copper coil 42 (which acts as a heat exchanger to increase the cooling power of the cooling compartment) to capillary tube 44 and exhaust tube 34 for thermal transfer of the fluid or gas. The oval shaped exhaust tube can also create sufficient space for disposition of the sensor (described below) that is disposed on the exhaust tube surface. The exhaust tube can have other shapes as well.

Figure 7:
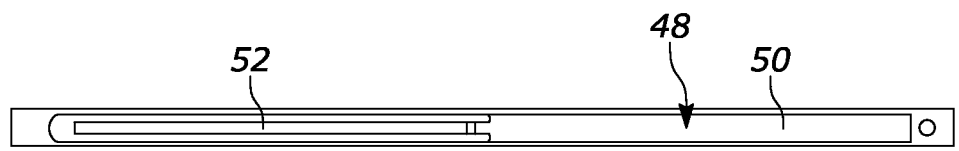
FIG. 7 is a top view of a heater cartridge of a heating compartment of a cryoablation probe according to an aspect of the present disclosure.
Figure 8:
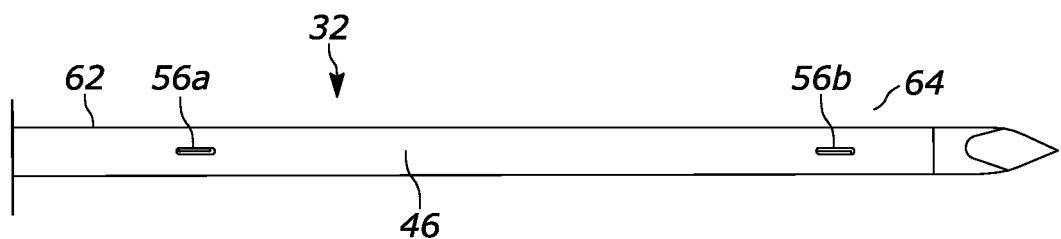
FIG. 8 is a side view of the heating compartment of a cryoablation probe according to an aspect of the present disclosure.

Referring back to FIG. 3, heating compartment 32 can comprise heater plate 46 and heater cartridge 48. Heater cartridge 48 can be located between exhaust tube 34 and heater plate 46. Heater cartridge can comprise a heater zone. Referring to FIG. 7, heater cartridge 48 can comprise at least two independently controlled heater zones 50 and 52 that can generate specific amounts of heat energy to mitigate or prevent ice formation on or about the heating compartment. Zone 50 can be located at a distal portion of the heater cartridge and zone 52 can be located at a proximal portion of the heater cartridge. Preferably the two or more zones are positioned longitudinally adjacent to each other such that there is not any or there is minimal amount of "unheated" heater cartridge space. The at least two zones may be necessary due to the different temperature gradients along the probe's longitudinal axis generated by the Joule Thomson effect. This can allow the minimum amount of heat to be applied by the heating compartment to prevent bridging while not interrupting the probe regenerative cycle by heating the outgoing gas or fluid. The heater cartridge can alternatively comprise a single heater zone with traces of variable widths such that the effect of two zones could be created. In other words, the heater traces can be configured to have smaller/larger widths to create the effect similar to having two zones. If the traces are smaller/thinner, then the heating would be greater. If the tracers are wider/thicker, then the heating would be less. As such, the trace width/ thickness can be modulated to emulate the variable resistance and thus variable heating generation within a single zone.

The heater cartridge can have a substantially concave configuration. The concave configuration is a result of using a round needle and positioning the heater as far away from the exhaust tube as possible. The heater cartridge can have other configurations as well. The heater plate can provide a rigid, smooth and atraumatic external surface for the heater cartridge and sensor (described below). Further, the heater plate can serve as a heat spreader to equalize the temperature across the at least two independently controlled zones. The heater plate can be fabricated from a stainless steel material, for example. The materials are also possible. The heater cartridge can comprise a constantan wire laminated between polyamide sheets but other materials are also possible.

A thermally insulating material can isolate the heating compartment and the cooling compartment and can minimize the amount of cooling energy that may flow to the heating compartment. The thermally insulating material can bias the cooling gradient towards the first side of the action region of the probe and maximize deposition of ice in the target tissue site. In particular and with reference to FIG. 4, in certain aspects, a layer 66 of a high thermal conductivity and low electrical conductivity material can be disposed between heater cartridge 48 and heater plate 46 (e.g. can be layered onto the inner surface of the heater plate) and a layer 68 of a low thermal conductivity and low electrical conductivity material can be disposed between heater cartridge (e.g. layered on the inner surface of the heater cartridge) 48 and exhaust tube 34. The materials can be an epoxy material to adhere the materials to the described components. As stated above, the high thermal conductivity and low electrical conductivity material adhered to the heater plate or otherwise disposed between the heater cartridge and the heater plate can bias the heater cartridge's thermal gradient out toward the heater plate and can minimize heat flow from the heating compartment to the cooling compartment. In other words, this high thermal conductivity and low electrical conductivity material can maximize the heating gradient outwards towards tissue which can minimize a negative impact the heater cartridge may have on ice formation. If too much heat goes from the heater cartridge to the exhaust tube, the size of the target ablation zone can be negatively impacted. Further, this high thermal conductivity and low electrical conductivity material can ensure sufficient heating of the heating compartment to prevent or mitigate ice formation at the heating compartment or transfer of thermal energy. The layer of a low thermal conductivity and low electrical conductivity material disposed between the heater cartridge and the exhaust tube can limit the transfer of hot/cold gradients within the probe. This material can fill the space between the heater cartridge and the exhaust tube. Such material between the heating compartment and cooling compartment promotes directionality of the cryozone (i.e ice formation). Without such material, the cooling power of the cooling compartment may overpower the heater cartridge such that cryozone directionality cannot be achieved. The heating compartment should only get as hot as clinically necessary without becoming unsafe and the low thermal conductivity and low electrical conductivity material can aid in ensuring this property.

Figure 9:
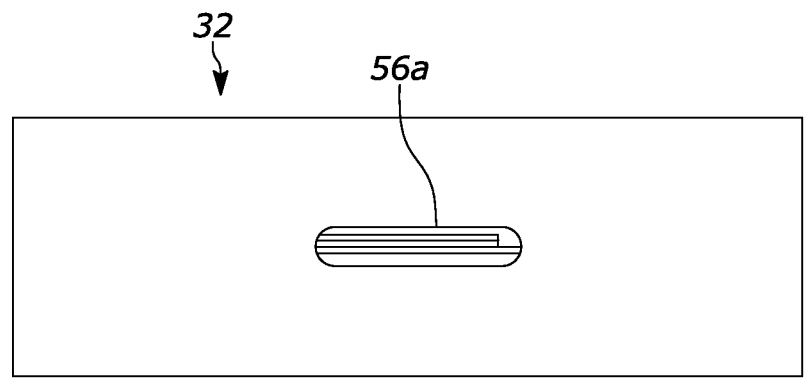
FIG. 9 is a close-up view of the proximal thermocouple wire of the heating compartment of FIG. 8.
Figure 10:
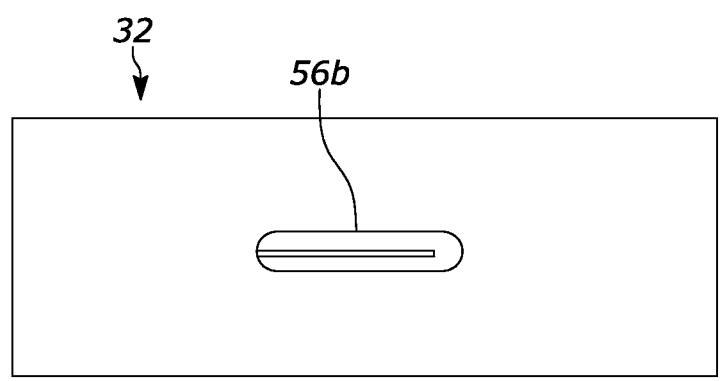
FIG. 10 is a close-up view of the distal thermocouple wire of the heating compartment of FIG. 8.

Referring FIGS. 3, and 8-10, cooling compartment 30 comprises at least one temperature sensor such as a proximal temperature sensor. The cooling compartment can alternatively comprise at least two temperature sensors 54a and 54b that can be disposed adjacent to exhaust tube 34. The heating compartment can comprise at least one temperature sensor such as a proximal temperature sensor. The heating compartment 32 can alternatively comprise at least two temperature sensors 56a and 56b that can be disposed adjacent to heater plate 46. The at least two temperature sensors 54a and 54b of cooling compartment 30 can be located at a proximal portion 58 and a distal portion 60 respectively of cooling compartment 30 and the at least two temperature sensors 56a and 56b of heating compartment 32 can be located at a proximal portion 62 and a distal portion 64 respectively of heating compartment 32. The temperature sensors can be thermocouple wires as illustrated in FIGS. 9 and 10. In particular, with respect to the cooling compartment, the distal sensor can be mounted on the outer surface of the exhaust tube and can be used to measure temperature between the cooling compartment and the heating compartment close to the capillary tube opening. This temperature can be used to verify maximum performance is being achieved by checking the rate of temperature cooling and to regulate heating and cooling to achieve directional cryozone formation. The proximal sensor can also be mounted on the outer surface of the exhaust tube between the cooling and heating compartment and can be used to measure temperature near the edge of the target ablation site before gas exhausts out of the active region of the probe. This temperature measurement can be used as well to verify maximum performance is being achieved by checking the rate of temperature cooling and to regulate the heating and cooling to achieve directional cryozone formation. With respect to the heating compartment, the distal sensor can be mounted between the heater plate and the heater cartridge within the epoxy layer. This distal sensor can be used to measure the temperature of the distal portion of the heating compartment. Trends in the heating profile can be used to detect ice formation outside of the target ablation site (i.e., bridging), regulate heating power, and ensure heating at a safe temperature. The proximal sensor can be used to measure the temperature of the proximal portion of the heating compartment and can also be used to monitor trends in the heating profile to detect ice formation outside of the target ablation site (i.e., bridging), regulate heating power, and ensure heating at a safe temperature.

The cryoablation system can further include a non-active region distal to the heater cartridge of the cryoablation probe comprising an insulated sleeve configured to prevent or minimize ice formation about the non-active region of the cryoablation probe. A portion of the exhaust tube proximal to the active region can be disposed in the insulated sleeve.

Figure 11:
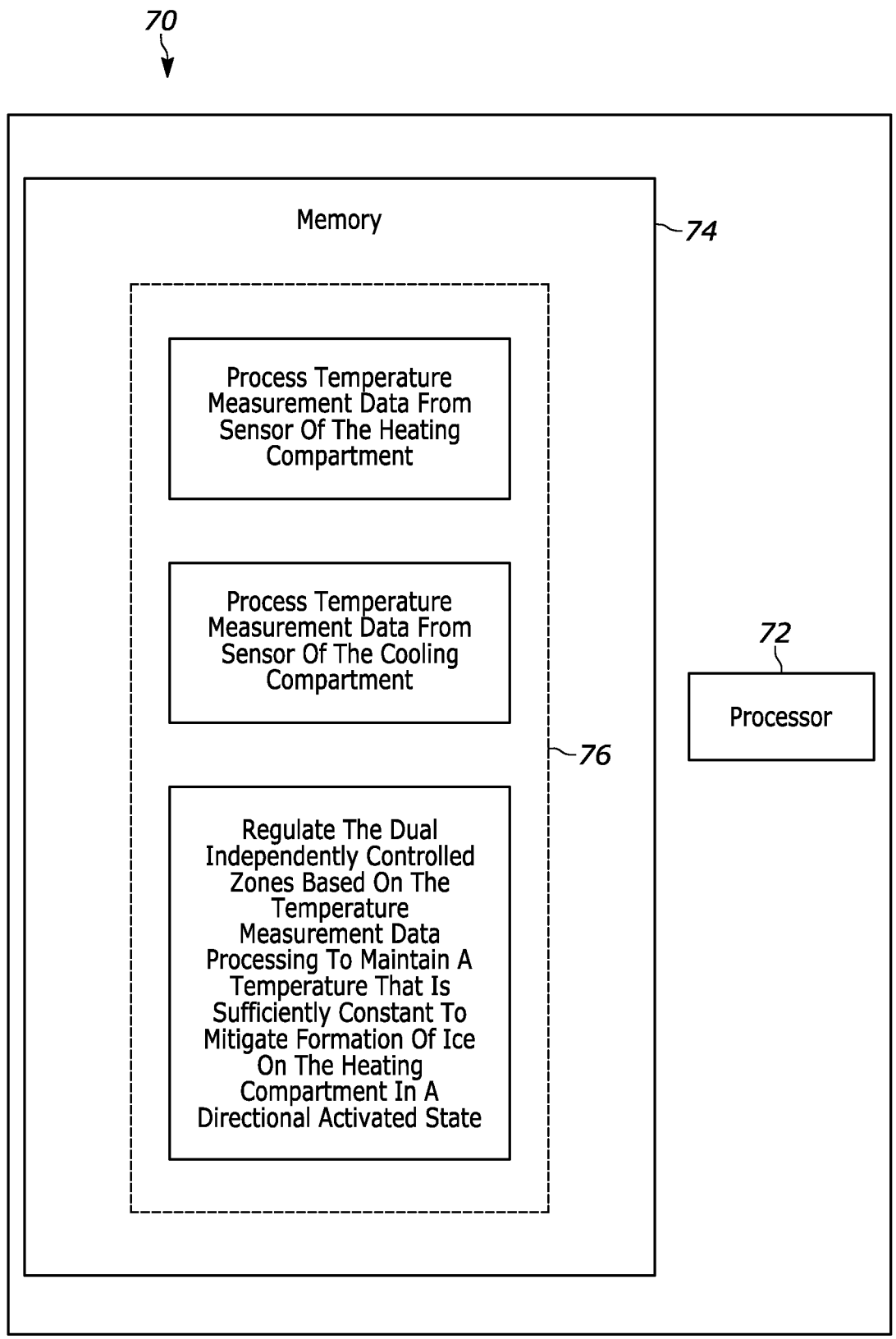
FIG. 11 is a block diagram depicting illustrative components of a controller of a cryoablation system according to an aspect of the present disclosure.

Referring to FIG. 11, the cryoablation system can include a controller 70 operably connected to the cryoablation probe and comprising a processor 72 and memory 74. Memory 74 can have computer-executable instructions 76 stored thereon that, when executed by processor 72 cause controller 70 to process temperature measurement data from the at least one sensor of the heating compartment and the at least one sensor of the cooling compartment. The instructions can also cause controller 70 to regulate the heater zone of the heater cartridge (or in certain embodiments at least two independently controlled zones 50 and 52 of heater cartridge 48) based on the temperature measurement data processing to maintain a temperature that is sufficiently constant to mitigate or prevent the formation of ice on the heating compartment in a directional activated state of the cryoablation system. In particular, the heater cartridge can be controlled by the controller to maintain a constant temperature at the probe surface. The thermocouples or other thermal sensors can be strategically positioned so that the controller, receiving temperature measurement data from the sensors, can prevent bridging and ensure the probe does not get hot enough to unintentionally burn tissue. Embodiments with at least two zones of the heater cartridge regulated by the controller are advantageous because the cooling energy produces an energy gradient along the axis of the probe, generally getting colder at the distal end. The distal heater cartridge zone generally draws twice the power of the proximal heater cartridge zone. The at least two heater zones can also allow the controller to regulate introduction of the minimum amount of heat to prevent bridging which reduces interference with the cryogenic cooling cycle.

The controller can be a proportional-integral-derivative (PID) controller. Using the sensors, tissue temperature measurements can be determined in real-time and relayed to the PID controller. The PID controller can, in turn, regulate the duty cycle of the gas/liquid flow and the heating array temperature to achieve the desired cryozone shape, size, and temperature. In particular, and in addition or in alternative to the instructions described above, the controller can have computer-executable instructions stored in the memory that, when executed by the processor, cause the controller to perform other steps. For example, such instructions can include monitoring bridging of ice about or on the cryoablation probe based on the temperature measurement data processing; identifying the time to deliver the gas or the fluid through the exhaust tube based on the temperature measurement data processing and identifying the time to heat the heating compartment based on the temperature measurement data processing; stopping the heating of the heating compartment or the fluid or the gas when a critical value has been reached based on the temperature measurement data processing; monitoring the rate of cooling by the cooling compartment and regulating the rate of cooling based on the temperature measurement data obtained from the proximal temperature sensor and the distal temperature sensor of the cooling compartment; monitoring the rate of heating by the heating compartment and regulating the rate of heating based on the temperature measurement data obtained from the proximal temperature sensor and the distal temperature sensor of the heating compartment; regulating the flow of the fluid or the gas through the exhaust tube based on the temperature measurement data processing; regulating the power level of the heating compartment (e.g. the heater zone including each of the at least two independently controlled zones of the heater cartridge) based on the temperature measurement data processing; and combinations thereof.

Memory 74 can include computer-readable instructions that, when executed by processor 72, cause the controller to perform various functions attributed throughout this disclosure to the controller. The computer-readable instructions can be encoded within memory 74. The memory can comprise non-transitory computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media with the sole exception being a transitory, propagating signal.

A non-limiting example of a protocol for generating directional ice formation can comprise delivering two minutes of gas or fluid with the heater power regulated using the temperature sensor measurements. In particular, the amount of time the gas or fluid is delivered can be dictated by the profile of the temperature sensor measurement data. The protocol can further comprise stopping delivery of the gas or fluid for 30 seconds with the heater cartridge power reduced by the profile of the temperature sensor measurement data. The cycle can be repeated for five times, for example, to produce the necessary size of ice. Such a protocol is only exemplary and other protocols can be used to generate a cryozone of the desired size, shape and configuration.

The cryoablation system can include other components such as a control console. The control console can serve many different functions. For example, it can regulate gas pressure and flow, supply power to the probe and in-console electronics, and house the probe position tracking circuitry as well as the computer and a touchscreen monitor. The control console can power and control more than one cryoablation probe at once. Argon gas, or another fluid or gas that exhibits a Joule Thomson cooling effect, can be attached to the console inlet port, flow through a regulator and dryer, and exit the console through gated valves that control gas flow through the probe. A power unit can be configured to provide sufficient power to all electronics embedded within the cryoablation probe. A microcontroller can monitor the entire system for compliance and safety.

The focused cryoablation system is well-suited for pain management versus heat modalities such as radiofrequency, microwave, laser, or ultrasound procedures, because the procedure produces less post-procedural pain or neuroma formation. The systems can be used to treat a variety of pain indications such as chronic abdominal pain (e.g. where the target nerves can be the splanchnic nerves, which have connections to the celiac plexus), phantom limb pain, pudendal neuralgia, and Inguinodynia. Other conditions include chronic disorders that result from abnormal nerve activity such as sexual dysfunction, tachycardia, diabetes, and obesity.

Each of the disclosed aspects and embodiments of the present disclosure may be considered individually or in combination with other aspects, embodiments, and variations of the disclosure. Further, while certain features of embodiments and aspects of the present disclosure may be shown in only certain figures or otherwise described in the certain parts of the disclosure, such features can be incorporated into other embodiments and aspects shown in other figures or other parts of the disclosure. Along the same lines, certain features of embodiments and aspects of the present disclosure that are shown in certain figures or otherwise described in certain parts of the disclosure can be optional or deleted from such embodiments and aspects. Additionally, when describing a range, all points within that range are included in this disclosure. Further, unless otherwise specified, none of the steps of the methods of the present disclosure are confined to any particular order of performance. Furthermore, all references cited herein are incorporated by reference in their entirety.

What is claimed is:

1. A cryoablation system having a directional activated state and a non-directional activated state, the cryoablation system comprising:
 a cryoablation probe to ablate a target site comprising:
  a shaft having an outer surface, an inner surface, a distal portion, a proximal portion, a first side, and a second opposing side;
  an active region at the distal portion of the shaft, the active region comprising a cooling compartment located at the first side of the shaft and a heating compartment located at the second opposing side, the cooling and heating compartments thermally insulated from one another to minimize energy losses therebetween such that ice is selectively formed at the target site in a directional activated state of the cryoablation system, wherein:

the cooling compartment comprises:
an exhaust tube comprising a capillary tube disposed therein and configured to guide a fluid or gas that exhibits a Joule Thomson cooling effect through the shaft;
a heat exchanger coil disposed over the capillary tube;
at least one temperature sensor disposed adjacent to the exhaust tube; and the heating compartment comprises:
a heater plate;
at least one temperature sensor disposed adjacent to the heater plate; and
a heater cartridge located between the exhaust tube and the heater plate and comprising a a heater zone; and a controller operably connected to the cryoablation probe, the controller comprising a processor and a memory, the memory having computer-executable instructions stored thereon that, when executed by the processor, cause the controller to:
process temperature measurement data from the at one temperature sensor of the heating compartment and the at least one temperature sensor of the cooling compartment; and
regulate the heater zone of the heater cartridge based on the temperature measurement data processing to maintain a temperature that is sufficiently constant to mitigate or prevent formation of ice on the heating compartment in a directional activated state of the cryoablation system.

2. The cryoablation system of claim 1, wherein the heater zone comprises at least two independently controlled heater zones and to regulate the heater zone comprises to regulate the at least two independently controlled heater zones.

3. The cryoablation system of claim 1, wherein the heater zone comprises a single heater zone with variable resistance and to regulate the heater zone comprises to regulate the single heater zone with variable resistance.

4. The cryoablation system of claim 1, wherein:
the at least one temperature sensor of the heating compartment comprises at least two temperature sensors;
the at least one temperature sensor of the cooling compartment comprises at least two temperature sensors; and
to process temperature measurement data comprises to process temperature measurement data from the at least two sensors of the heating compartment and the at least two sensors of the cooling compartment.

5. The cryoablation system of claim 4, wherein:
the at least two temperature sensors of the heating compartment comprise a proximal temperature sensor located at a proximal portion of the heating compartment and a distal temperature sensor located at a distal portion of the heating compartment; and
the at least two temperature sensors of the cooling compartment comprise a proximal temperature sensor located at a proximal portion of the cooling compartment and a distal temperature sensor located at a distal portion of the cooling compartment.

6. The cryoablation system of claim 5, further comprising computer-executable instructions stored in the memory, when executed by the processor, cause the controller to:
monitor the rate of cooling by the cooling compartment and regulate the rate of cooling based on the temperature measurement data obtained from the proximal temperature sensor and the distal temperature sensor of the cooling compartment; and
monitor the rate of heating by the heating compartment and regulate the rate of heating based on the temperature measurement data obtained from the proximal temperature sensor and the distal temperature sensor of the heating compartment.

7. The cryoablation system of claim 1, wherein the at least one temperature sensor of the heating compartment and the at least one temperature sensor of the cooling compartment are thermocouples.

8. The cryoablation system of claim 1, wherein the cooling compartment and the heating compartment are thermally insulated from one another such that ice is formed less than 360° degrees about the cryoablation probe in a directional activated state of the cryoablation system.

9. The cryoablation system of claim 1, further comprising:
a layer of a high thermal conductivity and low electrical conductivity material disposed between the heater cartridge and the heater plate; and
a layer of a low thermal conductivity and low electrical conductivity material disposed between the heater cartridge and the exhaust tube.

10. The cryoablation system of claim 9, wherein the high thermal conductivity and low electrical conductivity material is an epoxy and the low thermal conductivity and low electrical conductivity material is an epoxy.

11. The cryoablation system of claim 1, wherein the cooling compartment and the heating compartment are thermally insulated from one another such that a cryoablation temperature is generated only on the first side of the cryoablation probe when the cryoablation system is in a directional activated state.

12. The cryoablation system of claim 1, wherein the shaft at the first side of the cryoablation probe defines an open window, the exhaust tube disposed within the open window.

13. The cryoablation system of claim 1, wherein a central longitudinal axis extends through the shaft of the cryoablation probe, the heater cartridge being disposed radially outward from the central longitudinal axis.

14. The cryoablation system of claim 1, wherein the heating compartment and the cooling compartment are also sized and configured to generate circumferential formation of ice at the target site when the cryoablation system is in a non-directional activated state.

15. The cryoablation system of claim 1, further comprising computer-executable instructions stored in the memory that, when executed by the processor, cause the controller to monitor bridging of ice about or on the cryoablation probe based on the temperature measurement data processing.

16. The cryoablation system of claim 1, further comprising further comprising computer-executable instructions stored in the memory that, when executed by the processor, cause the controller to:
identify the time to deliver the fluid or the gas through the exhaust tube based on the temperature measurement data processing; and
identify the time to heat the heating compartment based on the temperature measurement data processing.

17. The cryoablation system of claim 1, further comprising computer-executable instructions stored in the memory that, when executed by the processor, cause the controller to stop heating of the heating compartment or the fluid or the gas when a critical value has been reached based on the temperature measurement data processing.

18. The cryoablation system of claim 1, further comprising computer-executable instructions stored in the memory that, when executed by the processor, cause the controller to regulate the flow of the fluid or the gas through the exhaust tube based on the temperature measurement data processing.

19. The cryoablation system of claim 1, further comprising computer-executable instructions stored in the memory that, when executed by the processor, cause the controller to regulate the power level of the heating compartment based on the temperature measurement data processing.

20. The cryoablation system of claim 1, further comprising a handle located at the proximal end of the proximal portion of the shaft, the handle comprising at least one electromagnetic sensor configured to track the position of the cryoablation probe.

\* \* \* \* \*